United States Patent
Choi et al.

(10) Patent No.: US 10,328,110 B2
(45) Date of Patent: *Jun. 25, 2019

(54) **PHARMACEUTICAL COMPOSITION FOR PROMOTING BONE TISSUE FORMATION, CONTAINING *STAUNTONIA HEXAPHYLLA* LEAF EXTRACT AS ACTIVE INGREDIENT**

(71) Applicants: Jeonnam Bioindustry Foundation, Naju-si, Jeollanam-do (KR); YUNGJIN PHARMACEUTICAL CO., LTD., Seoul (KR)

(72) Inventors: Chul Yung Choi, Gwangju (KR); Sang O Pan, Gwangju (KR); Hee Jin Seol, Gwangju (KR); Gyu Ok Lee, Jangheung-gun (KR); Wook Jin Jang, Jangheung-gun (KR); Hee Sook Kim, Goseong-gun (KR); Jae Yong Kim, Suncheon-si (KR); HuWon Kang, Naju-si (KR); Dong Wook Lee, Jangheung-gun (KR); Sun Oh Kim, Gwangju (KR); Jae Gap Kim, Bucheon-si (KR); JoonYung Park, Muan-gun (KR)

(73) Assignees: JEONNAM BIOINDUSTRY FOUNDATION, Naju-si (KR); YUNGJIN PHARMACEUTICAL CO., LTD., Seoul (KR)

( * ) Notice: Subject to any disclaimer, the term of this patent is extended or adjusted under 35 U.S.C. 154(b) by 4 days.

This patent is subject to a terminal disclaimer.

(21) Appl. No.: 14/889,006

(22) PCT Filed: Apr. 29, 2014

(86) PCT No.: PCT/KR2014/003742
§ 371 (c)(1),
(2) Date: Nov. 4, 2015

(87) PCT Pub. No.: WO2015/002378
PCT Pub. Date: Jan. 8, 2015

(65) Prior Publication Data
US 2016/0113979 A1  Apr. 28, 2016

(30) Foreign Application Priority Data
Jun. 30, 2013 (KR) .......................... 10-2013-0076190

(51) Int. Cl.
A61K 36/71 (2006.01)
A61K 36/185 (2006.01)
A23L 33/105 (2016.01)
A61K 9/16 (2006.01)
A61K 9/20 (2006.01)

(52) U.S. Cl.
CPC .......... *A61K 36/185* (2013.01); *A23L 33/105* (2016.08); *A61K 36/71* (2013.01); *A23V 2002/00* (2013.01); *A61K 9/16* (2013.01); *A61K 9/20* (2013.01)

(58) Field of Classification Search
CPC ..................................................... A61K 36/71
USPC ............................................................ 424/774
See application file for complete search history.

(56) References Cited

FOREIGN PATENT DOCUMENTS

| | | |
|---|---|---|
| JP | 2011-195532 A | 10/2011 |
| JP | 2011-201811 A | 10/2011 |
| KR | 10-1221617 B1 | 1/2013 |
| KR | 10-2013-0020095 A | 2/2013 |
| KR | 10-1243115 B1 | 3/2013 |
| KR | 10-1317668 B1 | 10/2013 |
| WO | WO 2012/133825 A1 | 10/2012 |

OTHER PUBLICATIONS

Wang et al. "A Phenolic Glycoside and Triterpenoids From Stauntonia Hexaphylla", Phytochemistry, vol. 47, No. 3, pp, 467-470, 1998.*
US. Department of Health and Human Services "What Is Bone Disease?", A Report of the Surgeon General, 2004.*
International Search Report, issued in PCT/KR2014/003742, dated Oct. 29, 2014.
Patent Examination Report No. 1 dated Sep. 2, 2016, in Australian Patent Application No. 2014284932.
Wang et al., "Bisepoxylignan Glycosides from *Stauntonia hexaphylla*," Phytochemistry, vol. 34, No. 6, pp. 1621-1624, 1993.
Wang et al., "Triterpenoid Glycosides from *Stauntonia hexaphylla*," Phytochemistry, vol. 34, No. 5, pp. 1389-1394, 1993.
Extended European Search Report dated Jan. 26, 2017 in Patent Application No. 14819974.8.

* cited by examiner

*Primary Examiner* — Christopher R Tate
*Assistant Examiner* — Deborah A Davis
(74) *Attorney, Agent, or Firm* — Birch, Stewart, Kolasch & Birch, LLP

(57) ABSTRACT

The present invention relates to a composition for promoting osteoblast or cartilage cell differentiation. More particularly, the present invention relates to a composition, which includes *stauntonia hexaphylla* leaf extract that may be safely used without toxicity and side effects by using a natural ingredient, for promoting bone (tissue) formation to be used for suppressing and treating bone and cartilage tissue damage. A pharmaceutical composition including the *stauntonia hexaphylla* leaf extract according to the present invention as an active ingredient may be used as a medicine for periodontitis or osteoporosis to treat or prevent periodontitis or osteoporosis.

6 Claims, 4 Drawing Sheets

[FIG. 1]
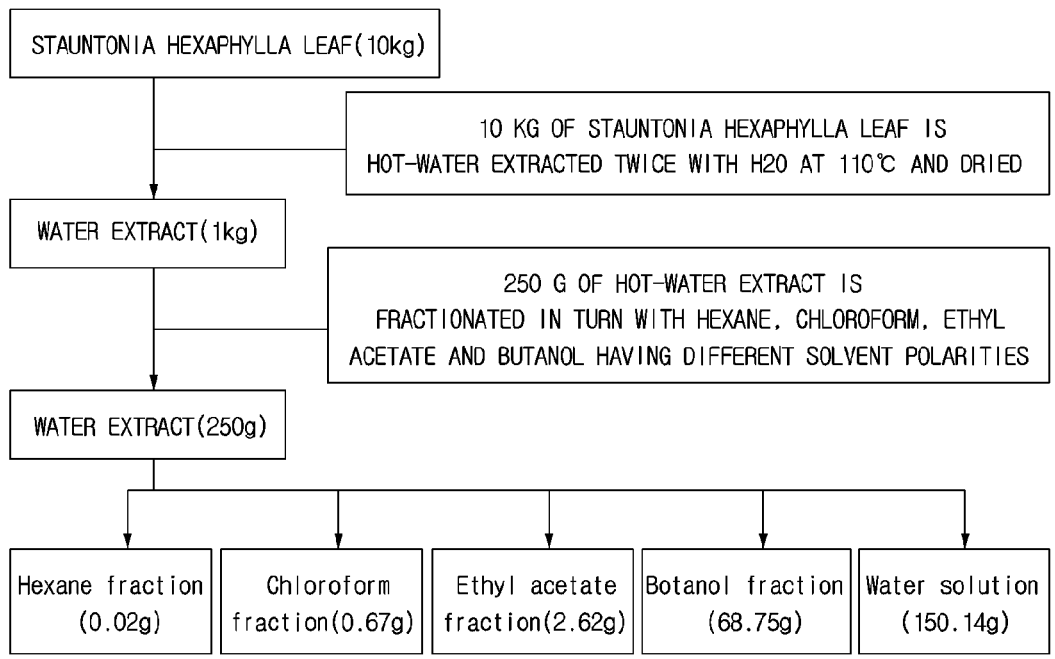

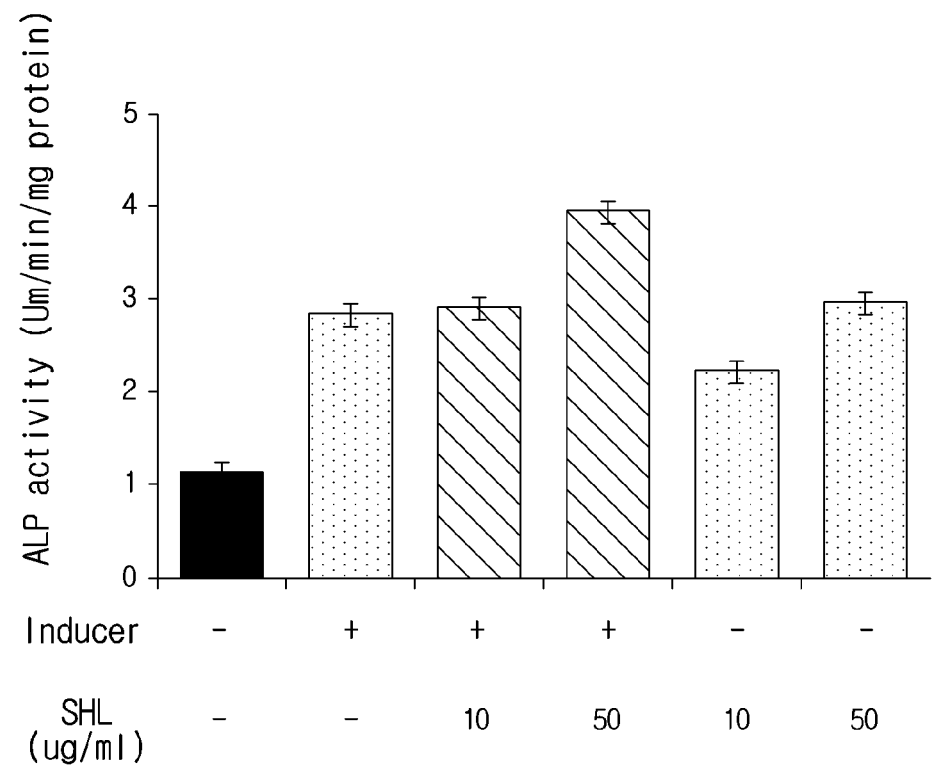
[FIG. 2]

[FIG. 3]
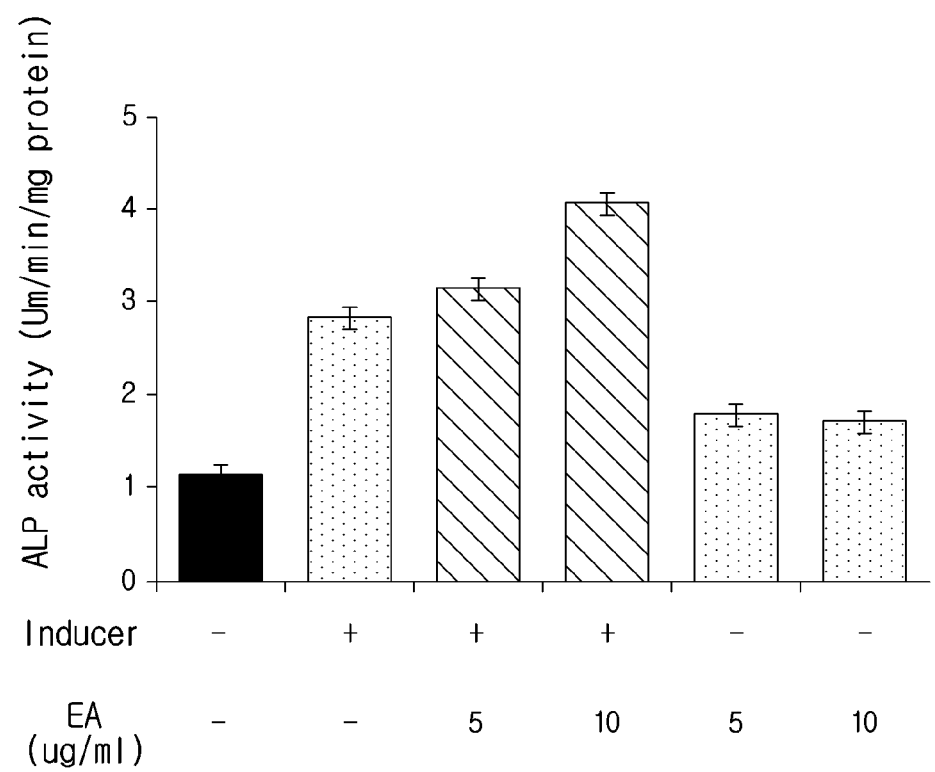

[FIG. 4]
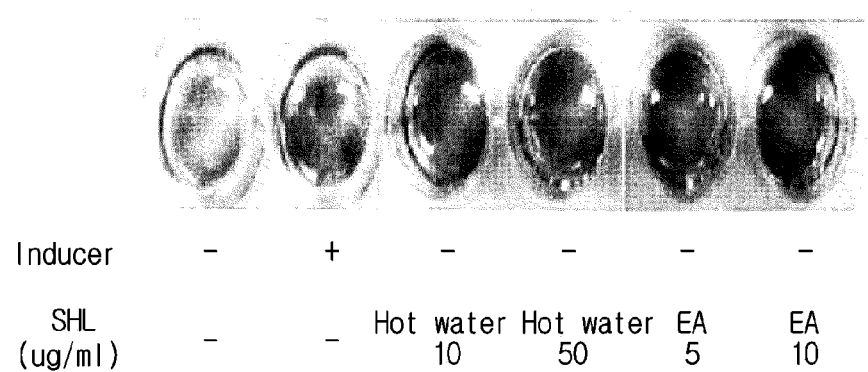

PHARMACEUTICAL COMPOSITION FOR PROMOTING BONE TISSUE FORMATION, CONTAINING *STAUNTONIA HEXAPHYLLA* LEAF EXTRACT AS ACTIVE INGREDIENT

TECHNICAL FIELD

The present invention relates to a pharmaceutical composition for promoting bone tissue formation. More particularly, the present invention relates to a pharmaceutical composition for promoting bone tissue formation, the pharmaceutical composition being used for safely suppressing and treating bone and cartilage tissue damage without toxicity and side effects using a natural ingredient including *stauntonia hexaphylla* leaf extract.

BACKGROUND ART

In general, bone tissue is mostly composed of dense bone tissue forming solid bone surfaces, and bone tissues of center parts thereof and both ends of long bones is composed of spongy bone tissue assembled like meshes. Most bones are first derived from cartilage as connective tissue and then change into bone tissues. Some bones thereof are directly formed from connective tissues.

There are articular surfaces in parts contacting neighboring bones of epiphyses. The surfaces are covered with articular cartilages as hyaline cartilages. Trabecula of spongiosum present in the middle of sponginess has constant arrangements. Wide medullary cavities of disphyseal parts are connected to lacunae composed of spongiosum trabecula and all thereof are filled with bone marrow.

Bone marrow performing hematopoiesis is reddish due to blood vessels present therein and, thus, also called red bone marrow. All of compact bone substances or spongy bone substances of bone tissues are composed of bone plates stacked to a thickness of 5 to 12 μm. In compact bone substances, bone layer plates (Haversian layer plates) stacked in a concentric circle form are arranged in several directions, and a Haversian canal is present at the center of each plate. Blood vessels pass through the Haversian canal.

Bone cells are arranged between bone layer plates, and thin cytoplasmic protrusions with irregular shapes are connected to other bone cells. Periostea with tough connective tissue characteristics are present in surfaces of bones, and nerves and blood vessels are distributed therein, thereby protecting bones and providing nutrients. When periostea are deficient, survival, neogenesis and regeneration of bones are negatively affected. Bone tissues include 20% water, 35% organic substances including cells and 45% inorganic substances, and organic substances provide constant elasticity in bones. According to age, inorganic substances (mainly, calcium phosphate) are increased, thereby increasing hardness of bones.

Meanwhile, *stauntonia hexaphylla* is a plant belonging to plantae, magnoliophyta, anthophyta, and ranales. *Stauntonia hexaphylla* is mainly distributed in Korea, Japan, Taiwan, China, etc. Main stems thereof extend to about 5 m, and leaves thereof are compound leaves which are crossed and have a palm shape composed of five small leaves. The small leaves are thick and have egg shapes or oval shapes, and edges thereof are flat. Leafstalks thereof are 6 to 8 cm and small leafstalks are 3 cm. Flowers thereof bloom May and are monoecious, yellow-white racemes.

Flower stems of female flowers become reddish-brown in the fall and are tough due to many lenticels. Fruits are ovoid or oval berries, and have a length of 5 to 10 cm. The fruits change reddish-brown in October and are more delicious than chocolate vine fruit. Seeds are black and have ovoid or oval shapes.

In the present invention, in order to prepare a pharmaceutical composition for treating or preventing periodontitis or osteoporosis using *stauntonia hexaphylla* leaf extract as a natural material, osteoblast ALP activity and osteoblast differentiation promotion experiments and bone or cartilage tissue generation promotion experiments are performed using *stauntonia hexaphylla* leaf hot-water extract or ethyl acetate fractions extracted from *stauntonia hexaphylla* leaf hot-water extract.

As experimental results, it was confirmed that *stauntonia hexaphylla* extract has effects on bone tissue generation promotion and bone tissue disease prevention, and thus, the present invention aims to provide a pharmaceutical composition and a medicine for bone generation promotion using *stauntonia hexaphylla* extract.

Korean Patent Application Pub. No. 10-2013-0020095 relates to a composition for liver protection, including *stauntonia hexaphylla* extract. It is confirmed that the *stauntonia hexaphylla* extract derived from an edible plant is free from side effects or safety issues, significantly suppresses lipid peroxidation in animal models treated with carbon tetrachloride or acetaminophen for liver toxicity experiments, inhibits GOT and GPT level increase in serum, and has effects on liver protection, liver damage prevention and liver function enhancement. Accordingly, a composition according to the present invention is applicable to pharmaceutical compositions for liver disease treatment or prevention, food compositions for liver function improvement or liver protection, or various applications related to fatigue recovery or hangover relief.

Korean Patent Application Pub. No. 10-11675890 relates to an anti-inflammatory composition including *stauntonia hexaphylla* fruit extract as an active ingredient. *Stauntonia hexaphylla* fruit extract is not cytotoxic, and, through results of mRNA transcription levels of cytokines and NO secretion amounts related to inflammation, it is confirmed that fruits among several parts of *stauntonia hexaphylla* most effectively inhibit inflammation. The application discloses an anti-inflammatory agent including *stauntonia hexaphylla* fruit extract, which may be used in anti-inflammatory agents inhibiting inflammation of diseases related to inflammation and cosmetic compositions having anti-inflammatory effects.

Korean Patent No. 10-1243115 discloses an antipyretic including *stauntonia hexaphylla* leaf extract, as an active ingredient, which is not cytotoxic and has superior antipyretic effects, compared to conventional antipyretics.

Korean Patent Application Pub. No. 10-1221617 relates to an anti-inflammatory composition including *stauntonia hexaphylla* leaf extract as an active ingredient. Particularly, disclosed is an anti-inflammatory agent including *stauntonia hexaphylla* leaf extract which is not cytotoxic and may effectively inhibit inflammation by lowering mRNA transcription levels of cytokines related to inflammation and NO secretion amounts and inhibiting a COX-2 enzyme causing inflammation.

However, the related art differs from the present invention in that, in the present invention, ethyl acetate fractions are extracted from *stauntonia hexaphylla* leaf hot-water extract or *stauntonia hexaphylla* leaf hot-water extract in order to use *stauntonia hexaphylla* leaf extract, as a natural material, as a pharmaceutical composition for treating or preventing periodontitis or osteoporosis, and the extracted fractions are used as compositions for bone generation promotion, effects thereof are confirmed through osteoblast ALP activity and osteoblast differentiation promotion experiments and bone or cartilage tissue generation promotion experiments.

DISCLOSURE

Technical Problem

Therefore, the present invention has been made in view of the above problems, and it is an object of the present invention to provide a pharmaceutical composition including *stauntonia hexaphylla* leaf extract promoting bone tissue generation to be used for safely suppressing and treating bone and cartilage tissue damage without side effects even when *stauntonia hexaphylla* leaf extract, as a natural substance, as an active ingredient is taken for a long time.

Technical Solution

In accordance with an aspect of the present invention, the above and other objects can be accomplished by the provision of a pharmaceutical composition, which includes *stauntonia hexaphylla* leaf crude extract or nonpolar soluble extract as an active ingredient, for promoting bone tissue generation to be used for suppressing or treating bone and cartilage tissue damage.

The *stauntonia hexaphylla* leaf extract may be an extract in any one of water, methanol, ethanol, propanol, isopropanol, butanol or solvent mixtures thereof. A nonpolar solvent may be any one selected from hexane, chloroform, dichloromethane and ethyl acetate.

The *stauntonia hexaphylla* leaf hot-water extract may increase activities of ALP generated in osteoblasts and osteoblast differentiation, and ethyl acetate fractions of the *stauntonia hexaphylla* leaf hot-water extract may increase activity of ALP generated in osteoblasts and osteoblast differentiation.

In addition, the *stauntonia hexaphylla* leaf extract may be included in an amount of 0.01 to 99.9% by weight based on the total amount of pharmaceutical compositions, and a daily dose of the pharmaceutical composition may be 10 to 1000 mg per kg of body weight.

Advantageous Effects

A pharmaceutical composition including *Stauntonia hexaphylla* leaf hot-water extract and ethyl acetate fractions of *stauntonia hexaphylla* leaf hot-water extract according to the present invention as active ingredients promotes bone or cartilage tissue generation by promoting ALP activity and osteoblast differentiation and thus may be used as a medicine for treating or preventing periodontitis or osteoporosis.

DESCRIPTION OF DRAWINGS

FIG. 1 is a schematic view illustrating a process of preparing *stauntonia hexaphylla* leaf hot-water extract and fractions;

FIG. 2 is a graph illustrating influence of *stauntonia hexaphylla* leaf hot-water extract on ALP activity (bone formation promotion through osteoblast differentiation);

FIG. 3 is a graph illustrating influence of *stauntonia hexaphylla* leaf hot-water extract ethyl acetate fractions on ALP activity; and FIG. 4 illustrates staining results showing ALP activity of *stauntonia hexaphylla* leaf hot-water extract and ethyl acetate fractions from *stauntonia hexaphylla* leaf hot-water extract.

BEST MODE

The present invention provides a pharmaceutical composition, which includes *stauntonia hexaphylla* leaf extract or a nonpolar soluble extract as active ingredients, for bone tissue generation promotion to be used for suppressing and treating bone and cartilage tissue damage, and a medicine for periodontitis or osteoporosis including the same.

1. Preparation of *Stauntonia Hexaphylla* Leaf Hot-water Extract

FIG. 1 illustrates a schematic view regarding a preparation process of *stauntonia hexaphylla* leaf hot-water extract and fractions. 10 kg of *stauntonia hexaphylla* (*stauntonia hexaphylla*) leaves were washed with distilled water and then 200 L of distilled water was added thereto, followed by extracting through heating for four hours at 110° C. by means of an electric medicine porter. Filtration was performed by means of a 400 mesh tamis and then concentration was performed by means of a vacuum rotary concentrator. After filtration, remainders were extracted twice or more with the same amount of distilled water in the same manner, and were subject to filtration and vacuum concentration. The concentrated hot-water extract was freeze-dried by means of a freeze dryer. Thereby, 1 kg of *stauntonia hexaphylla* leaf hot-water extract (10%) was obtained.

2. Preparation of *Stauntonia Hexaphylla* Leaf Fractions Soluble in Polar Solvent and Nonpolar Solvents As illustrated in FIG. 1, prepared *stauntonia hexaphylla* leaf hot-water extract was fractionated using an organic solvent as follows.

2.1. Isolation of Soluble Hexane Fractions 250 g of obtained *stauntonia hexaphylla* leaf extract was completely dissolved in 5 L of distilled water and then input to a separatory funnel. 5 L of hexane was input to the separatory funnel to separate an insoluble hexane layer (water layer) and a soluble hexane layer. Using the insoluble hexane layer (water layer), the same process was repeated three times, collecting insoluble and soluble fractions.

2.2. Isolation of Soluble Chloroform Fractions

5 L of chloroform was added to insoluble hexane fractions (water layer), followed by mixing. Subsequently, soluble and insoluble chloroform fractions were separated. Using the insoluble chloroform layer (water layer), the same process was repeated three times, collecting insoluble chloroform fractions and soluble chloroform fractions.

2.3. Isolation of Soluble Ethyl Acetate Fractions

5 L of ethyl acetate was added to insoluble chloroform fractions (water layer), followed by mixing. Subsequently, soluble and insoluble ethyl acetate fractions were separated. Using an insoluble ethyl acetate layer (water layer), the same process was repeated three times, collecting insoluble and soluble ethyl acetate fractions.

2.4. Isolation of Soluble Butanol Fractions

5 L of butanol was added to insoluble ethyl acetate fractions (water layer), followed by mixing. Subsequently, soluble and insoluble butanol fractions were separated. Using an insoluble butanol layer, the same process was repeated three times, collecting insoluble and soluble butanol fractions.

2.5. Isolation of Water-layer Fractions 250 g of *stauntonia hexaphylla* leaf hot-water extract was completely dissolved in 5 L of distilled water, followed by inputting to a separatory funnel. Through the separatory funnel, the soluble hexane layer, a soluble chloroform layer, soluble ethyl acetate layer and a soluble butanol layer were fractionated. Subsequently, a remaining organic solvent was removed through concentration, and water fractions were collected.

Using 250 of the *stauntonia hexaphylla* leaf hot-water extract prepared through the *stauntonia hexaphylla* leaf hot-water extraction process and the fractioning process, soluble hexane fractions, soluble chloroform fractions, soluble ethyl acetate fractions and soluble butanol fractions were vacuum-concentrated, followed by freeze-drying. As a result, 0.02 g (0.015) of hexane fractions, 0.67 g (0.27%) of chloroform fractions, 2.62 g (1.05%) of ethyl acetate fractions, 68.75 g (27.5%) of butanol fractions, 150.14 g (60.06%) of water fractions were obtained and used as a sample.

3. Measurement of AP and ALP Activity in Osteoblasts by *Stauntonia Hexaphylla* Leaf Hot-water Extract FIG. 2 illustrates a graph showing influence of *stauntonia hexaphylla* leaf hot-water extract on ALP activity (bone formation promotion through osteoblast differentiation).

3.1 Measurement of AP Activity of Osteoblasts by *Stauntonia Hexaphylla* Leaf Hot-water Extract Since osteoblasts exhibit ALP activity, influence of the obtained *stauntonia hexaphylla* leaf hot-water extract on ALP activity of osteoblasts was measured. In particular, $C_2C_{12}$ cells as osteoblast stem cells were aliquoted to a 48 well plate in a number of $5 \times 10^4$ cells/well and cultured in α-MEM essential medium, as cell growth medium, containing 10% of FBS and 0.1% of p/s for three days. Three days later, the medium was changed with α-MEM essential medium including 1% horse serum and 0.1% p/s in order to induce osteoblast differentiation. Subsequently, the cells were treated with 10 ng/ml of BMP-2 (bone morphogenic protein-2), and samples were simultaneously treated in concentrations of and 50 ug/ml, followed by culturing for five days. Subsequently, the cells were treated with an AP assay buffer (kit) including 0.01% Triton X, and a sample necessary for ALP activity measurement was obtained by centrifuging at 1000× g for five minutes.

Using ALP decomposing p-nitrophenylphosphate into p-nitrophenol and phosphate, ALP activity was measured through absorbance changes at 405 nm. Protein concentrations were measured using a BioRad protein analysis kit. ALP activity was represented by PNP uM/min/mg protein.

3.2. Measurement of ALP Activity in Osteoblasts by *Stauntonia Hexaphylla* Leaf Hot-water Extract The *stauntonia hexaphylla* leaf hot-water extracts obtained through the *stauntonia hexaphylla* leaf hot-water extraction process and fractioning process were added to osteoblast stem cells ($C_2C_{12}$ cells) in concentrations of 10 and 50 ug/ml, respectively. The treated cells were cultured for four days and then influence thereof on ALP activity of osteoblasts was measured. Results are illustrated as a graph in FIG. 2. As illustrated in FIG. in the case of an experimental group in which BMP-2 and *stauntonia hexaphylla* leaf hot-water extract (10, 50 ug/ml) are simultaneously treated, ALP activity thereof increases in a concentration-dependent manner, compared a control treated with BMP-2.

In addition, when the *stauntonia hexaphylla* leaf hot-water extract (10, 50 ug/ml) is treated alone, ALP activity increases in a concentration-dependent manner, compared to a control not treated with BMP-2. Such results show that ALP activity increase by the *stauntonia hexaphylla* leaf hot-water extract has effects on direct osteoblast differentiation and bone formation promotion by activity increase since activity increase of ALP as an enzyme released by differentiation of osteoblasts and activity increase is directly related to osteoblast activity and increase thereof.

4. Measurement of AP and ALP Activity in Osteoblasts by Ethyl Acetate Fractions from *Stauntonia Hexaphylla* Leaf Hot-water Extract FIG. 3 is a graph illustrating influence of ethyl acetate fractions from *stauntonia hexaphylla* leaf hot-water extract on ALP activity.

4.1 Measurement of AP Activity of Osteoblasts by Ethyl Acetate Fractions from *Stauntonia Hexaphylla* Leaf Hot-water Extract Since osteoblasts exhibit ALP activity, influence of ethyl acetate fractions from the obtained *stauntonia hexaphylla* leaf hot-water extract on ALP activity of osteoblasts was measured. In particular, $C_2C_{12}$ cells as osteoblast stem cells were aliquoted to a 48 well plate in a number of $5 \times 10^4$ cells/well and cultured in α-MEM essential medium, as cell growth medium, containing 10% of FBS and 0.1% of p/s for three days.

Three days later, the medium was changed with α-MEM essential medium including 1% horse serum and 0.1% p/s in order to induce osteoblast differentiation. Subsequently, the cells were treated with 10 ng/ml of BMP-2 (bone morphogenic protein-2), and simultaneously treated with HP-20 column-eluted HP20-2 of butanol fractions from *stauntonia hexaphylla* leaf hot-water extract in concentrations of 10 and 50 ug/ml, respectively, followed by culturing for five days. Subsequently, the cells were treated with an AP assay buffer (kit) including 0.01% Triton X, and a sample necessary for ALP activity measurement was obtained by centrifuging at 1000× g for five minutes.

Using ALP decomposing p-nitrophenylphosphate into p-nitrophenol and phosphate, ALP activity was measured through absorbance changes at 405 nm. Protein concentrations were measured using a BioRad protein analysis kit. ALP activity was represented by PNP uM/min/mg protein.

4.2 Measurement of AP Activity in Osteoblasts by Ethyl Acetate Fractions of *Stauntonia Hexaphylla* Leaf Hot-water Extract Ethyl acetate fractions (5, 10 ug/ml) from the *stauntonia hexaphylla* leaf hot-water extracts were respectively to osteoblast stem cells ($C_2C_{12}$ cells) in concentrations of 10 and 50 ug/ml, respectively. The treated cells were cultured for four days and then influence thereof on ALP activity of osteoblasts was measured. Results are illustrated as a graph in FIG. 3. As illustrated in FIG. 3, in the case of an experimental group in which BMP-2 and the ethyl acetate fractions (10, 50 ug/ml) of *stauntonia hexaphylla* leaf hot-water extract are simultaneously treated, ALP activity thereof increases in a concentration-dependent manner, compared to a control treated with BMP-2.

In addition, when the ethyl acetate fractions (10, 50 ug/ml) of *stauntonia hexaphylla* leaf hot-water extract are treated alone, ALP activity increases in a concentration-dependent manner, compared to a control not treated with BMP-2. Such results show that ALP activity increase by the ethyl acetate fractions of *stauntonia hexaphylla* leaf hot water extract according to the present invention has effects on direct osteoblast differentiation and bone formation promotion by activity increase since activity increase of ALP as an enzyme released by differentiation of osteoblasts and activity increase is directly related to osteoblast activity and increase thereof.

4.3 Staining to Measure AP Activity in Osteoblasts by Ethyl Acetate Fractions from *Stauntonia Hexaphylla* Leaf Hot-water Extract $C_2C_{12}$ cells as osteoblast stem cells were aliquoted to a 48 well plate in a number of $5\times10^4$ cells/well and cultured in α-MEM essential medium, as cell growth medium, containing 10% of FBS and 0.1% of p/s for three days. Three days later, the medium was changed with α-MEM essential medium including 1% horse serum and 0.1% p/s in order to induce osteoblast differentiation. Subsequently, the cells were treated with 10 ng/ml of BMP-2 (bone morphogenic protein-2), and samples were simultaneously treated in a concentration-dependent manner, followed by culturing for five days.

In the present invention, groups were classified into a positive control treated with BMP-2 (10 ng/ml) as an osteoblast differentiation inducer, an experimental group treated with ethyl acetate fractions from *stauntonia hexaphylla* leaf hot-water extract (5, 10 ug/ml) alone and a non-treated control group none-treated, osteoblast differentiation degrees thereof were respectively measured through AP activity site staining using an NBT/BCIP substrate.

In particular, media of cells cultured for five days were removed and the cells were washed with 1× PBS three times. The cells were fixed at room temperature for 15 minutes by means of a 10% formalin solution and washed with 1× PBS three times to remove a formalin remainder. The cells were re-washed with a 1× alkaline phosphate solution, and then, AP activity sites thereof were stained with an NBT/BCIP substrate solution.

FIG. 4 illustrates ALP activity staining results for groups with *stauntonia hexaphylla* leaf hot-water extract and ethyl acetate fractions of *stauntonia hexaphylla* leaf hot-water extract. As illustrated in FIG. 4, it can be confirmed that, in the case of the positive control treated with BMP-2 alone, cells are more stained with NBT/BCIP, compared to the control group not treated with BMP-2 and the sample.

It can be confirmed that, in the case of the experimental group treated with the ethyl acetate fractions (5, 10 ug/ml) of *stauntonia hexaphylla* leaf hot-water extract alone, cells are more stained with NBT/BCIP, compared to the control group not treated with BMP-2 and the sample.

Since ALP is an enzyme released by differentiation and activity increase of osteoblasts and thus ALP activity increase is directly related to osteoblast activity and increase thereof, it can be considered that ALP activity increase by the ethyl acetate fractions of the *stauntonia hexaphylla* leaf hot-water extract according the present invention causes bone formation promotion effects through direct osteoblast differentiation and activity increase.

5. Pharmaceutical Composition for Bone and Cartilage Tissue Generation Promotion and Medicine for Preventing Periodontitis or Osteoporosis, including *Stauntonia Hexaphylla* Leaf Extract as an Active Ingredient A medicine including a pharmaceutical composition for promoting bone or cartilage tissue formation, for preventing or treating periodontitis or osteoporosis may be formulated in a form of a powder, a granule, a tablet, a capsule, a suspension, an emulsion, a syrup, an aerosol, an epidermal formulation, a suppository or a sterile injection solution such that the composition is included in an amount of 0.01 to 99.9% by weight.

In the case of the sterile injection solution, the pharmaceutical composition may be included in an amount of 0.01 to 99.9% by weight and mixed with 99.9 to 0.01% by weight of distilled water or glucose. In the case of the capsule, the pharmaceutical composition may be freeze-dried to be included in an amount of 0.01 to 99.9% by weight and mixed with 99.9 to 0.01% by weight of vitamins or calcium.

A daily administration amount of the prepared pharmaceutical composition includes the extract in an amount of 10 to 1000 mg per kg of body weight.

In addition, functional heath foods for enhancing or preventing periodontitis or osteoporosis including 0.01 to 99.9% by weight of the pharmaceutical composition may be prepared.

INDUSTRIAL APPLICABILITY

Since *stauntonia hexaphylla* leaf hot-water extract and ethyl acetate fractions from *stauntonia hexaphylla* leaf hot-water extract according to the present invention is confirmed as promoting bone or cartilage tissue generation by promoting osteoblast ALP activity and osteoblast differentiation, a pharmaceutical composition including the *stauntonia hexaphylla* leaf extract as an active ingredient may be used as a medicine for treating or preventing periodontitis or osteoporosis. In addition, production costs may be reduced since a plant from nature is used as a raw material, and, through industrialization thereof, import substitution and export effects may be anticipated.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A pharmaceutical composition for promoting bone or cartilage tissue formation consisting of a *stauntonia hexaphylla* fraction as an active ingredient that is made by extracting *stauntonia hexaphylla* leaf by boiling in water at 110° C. for 4 hours, separating into hexane soluble and insoluble layer, and using ethyl acetate to fractionate the hexane insoluble layer; and a pharmaceutically acceptable carrier.

2. The pharmaceutical composition according to claim 1, wherein the composition is comprised in an amount of 0.01 to 99.9% by weight.

3. The pharmaceutical composition according to claim 2, wherein a daily dose of the extract is 10 to 1000 mg per kg of body weight.

4. The pharmaceutical composition according to claim 2, wherein the composition is formulated in a form such as a powder, a granule, a tablet, a capsule, a suspension, an emulsion, a syrup, an aerosol, an epidermal formulation, a suppository or a sterile injection solution.

5. The pharmaceutical composition according to claim 1, wherein the extract is used for treating osteoporosis.

6. A functional heath food for enhancing osteoporosis, comprising 0.01 to 99.9% by weight of the pharmaceutical composition according to claim 1.

* * * * *